United States Patent
Erhart et al.

(10) Patent No.: US 9,247,975 B2
(45) Date of Patent: Feb. 2, 2016

(54) BONE SCREW SET

(75) Inventors: Jochen Erhart, Klosterneuburg (AT); Ewald Unger, Vienna (AT); Winfried Mayr, Moedling (AT)

(73) Assignee: MEDIZINISCHE UNIVERSITAET WIEN, Vienna (AT)

( * ) Notice: Subject to any disclaimer, the term of this patent is extended or adjusted under 35 U.S.C. 154(b) by 67 days.

(21) Appl. No.: 13/059,663

(22) PCT Filed: Aug. 20, 2009

(86) PCT No.: PCT/AT2009/000321
§ 371 (c)(1),
(2), (4) Date: May 10, 2011

(87) PCT Pub. No.: WO2010/019979
PCT Pub. Date: Feb. 25, 2010

(65) Prior Publication Data
US 2011/0208252 A1 Aug. 25, 2011

(30) Foreign Application Priority Data
Aug. 20, 2008 (AT) ................. A 1293/2008

(51) Int. Cl.
*A61B 17/86* (2006.01)
*A61B 17/17* (2006.01)
*A61B 17/88* (2006.01)

(52) U.S. Cl.
CPC ........... *A61B 17/863* (2013.01); *A61B 17/1735* (2013.01); *A61B 17/8875* (2013.01); *A61B 2017/8655* (2013.01)

(58) Field of Classification Search
CPC ...... A61B 17/84; A61B 17/844; A61B 17/86; A61B 17/8605; A61B 17/8625; A61B 17/863; A61B 17/8645; A61B 17/8685; F16B 35/005; F16B 35/02; F16B 35/04; F16B 35/041; F16B 35/06
USPC .......................... 606/300–323, 325–328, 64; 411/214–217, 75, 76, 307, 383–385; 623/13.14
See application file for complete search history.

(56) References Cited

U.S. PATENT DOCUMENTS

| | | | | |
|---|---|---|---|---|
| 1,017,371 | A * | 2/1912 | Beck | 411/321 |
| 5,984,681 | A * | 11/1999 | Huang | 433/174 |
| 6,013,078 | A * | 1/2000 | Lin | 606/308 |
| 6,030,162 | A * | 2/2000 | Huebner | 411/413 |

(Continued)

FOREIGN PATENT DOCUMENTS

| EP | 1 825 826 A1 | 8/2007 |
|---|---|---|
| FR | 2 655 840 A1 | 6/1991 |

(Continued)

*Primary Examiner* — Kevin T Truong
*Assistant Examiner* — Tracy Kamikawa
(74) *Attorney, Agent, or Firm* — Joyce von Natzmer; Agris & von Natzmer LLP

(57) ABSTRACT

The invention relates to a bone screw set for fixing two bone fragments, especially for treating a scaphoid bone fracture or a scaphoid bone pseudoarthrosis, comprising a first bone screw (1) and at least one second bone screw (2). The first bone screw (1) is preferably embodied as a compression screw, and the first and second bone screws (1, 2) comprise interacting engagement means for fixing the second bone screw (2) in a position, in relation to the first bone screw (1), wherein at least part of the second bone screw protrudes from the cross-section of the first bone screw (1).

11 Claims, 5 Drawing Sheets

(56) References Cited

U.S. PATENT DOCUMENTS

Figure 1:
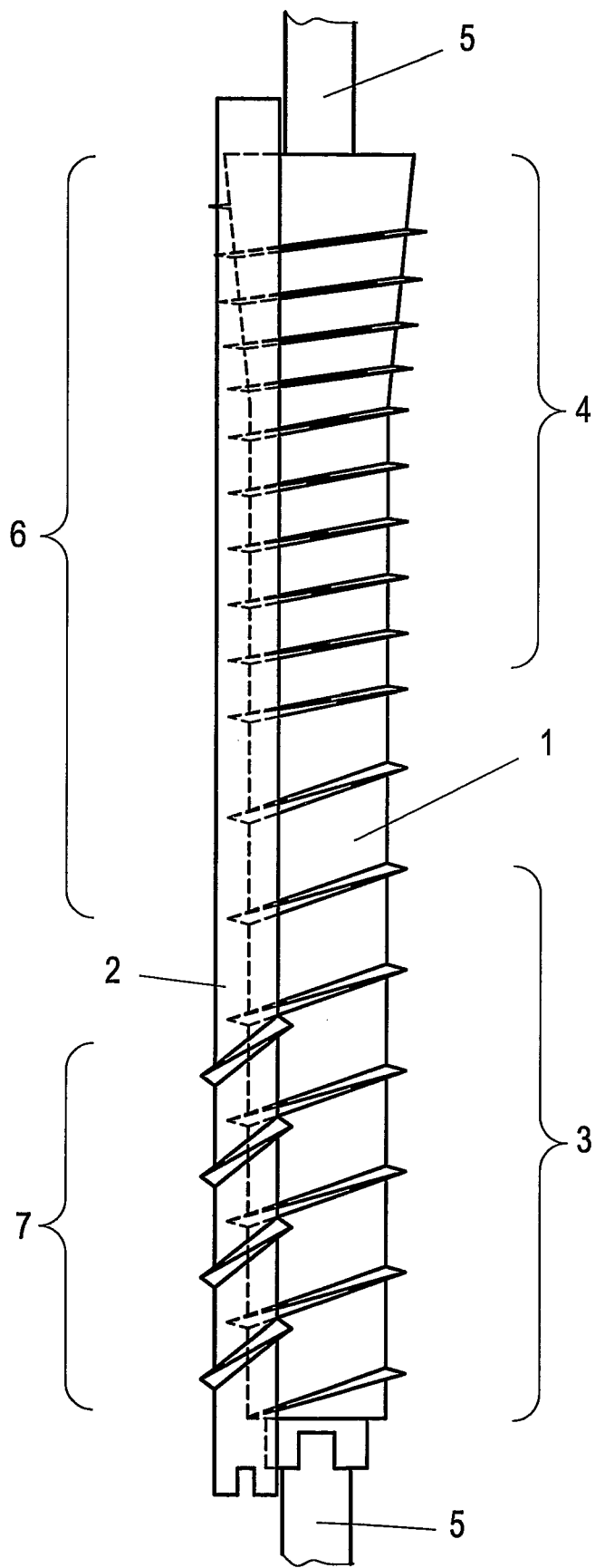

| | | | |
|---|---|---|---|
| 6,306,140 B1* | 10/2001 | Siddiqui | 606/315 |
| 6,468,277 B1* | 10/2002 | Justin et al. | 606/65 |
| 8,147,546 B2* | 4/2012 | Stone et al. | 623/13.14 |
| 2003/0135216 A1* | 7/2003 | Sevrain | 606/73 |
| 2004/0210227 A1* | 10/2004 | Trail et al. | 606/73 |
| 2005/0107791 A1* | 5/2005 | Manderson | 606/62 |
| 2005/0149024 A1* | 7/2005 | Ferrante et al. | 606/62 |
| 2006/0030852 A1* | 2/2006 | Sevrain | 606/73 |
| 2008/0051790 A1* | 2/2008 | Defossez | 606/64 |
| 2008/0188896 A1 | 8/2008 | Sevrain | |
| 2008/0233539 A1* | 9/2008 | Rossler et al. | 433/174 |
| 2010/0274296 A1* | 10/2010 | Appenzeller et al. | 606/305 |

FOREIGN PATENT DOCUMENTS

| | | |
|---|---|---|
| WO | 94/16636 A1 | 8/1994 |
| WO | 00/38586 A1 | 7/2000 |
| WO | 2007/109302 A2 | 9/2007 |
| WO | 2009/044395 A2 | 4/2009 |

* cited by examiner

BONE SCREW SET

This is the U.S. national stage of International application PCT/AT2009/000321, filed Aug. 20, 2009 designating the United States and claims priority to Austrian Patent No. A 1293/2008, filed Aug. 20, 2008.

The invention relates to a bone screw set for fixing two bone fragments, in particular for treating a scaphoid fracture or a scaphoid pseudoarthrosis, comprising a first bone screw and at least one second bone screw or a fixable pin as an anti-rotation element during torsional stress of the bone fragments to be connected.

The invention further relates to a method for fusing two bone fragments, in particular for treating a scaphoid fracture or a scaphoid pseudoarthrosis, using a bone screw set of this type.

The treatment of bone fractures frequently calls for an internal fixing of the bone fragments in the desired position. For this purpose a number of fixing means have already been proposed, which comprise, among other things, medullary pins, drill wires, plates and screws.

The screws that are used for fixing bone fragments are often embodied as compression screws. If a complete recessing of the compression screw into the bone is necessary, the implant must have threads with different screw pitches in different axial partial regions. When the different thread regions engage in the bone fragments to be connected to one another, a relative movement of the bone fragments with respect to one another and consequently a compression of the bone fragments to one another is effected by screwing the compression screw in further. The disadvantage in the isolated use of these compression screws, however, is that only one fixing of the bone fragments in the axial direction of the inserted screw is possible and the bone fragments are not secured against rotation about the screw axis. Although fixing means are known which, in addition, render possible a fixing about the rotational axis of the implant by means of transverse bores and by splints guided through these transverse bores, this type of securing cannot easily be applied in the case of smaller bones and under certain anatomical conditions. Specifically in the case of a scaphoid fracture, a minimally invasive operation with only one access to be kept as small as possible is desirable. A dissection of the soft parts, which would be necessary in order to insert guided transverse splints into transverse bores, is to be avoided not least because of compromising the specific blood supply of the scaphoid bone. A dissection of capsule and ligaments of the wrist with corresponding post-operative disadvantages would also be a prerequisite for this type of stabilization. In particular in the case of scaphoid pseudoarthrosis of the scaphoid bone, the splints (transverse bolts) would have to be placed via often only very small portions of the scaphoid bone supporting the joint, which furthermore have to act as important load transferers.

A rotationally stable traction screw osteosynthesis via one and the same access is desirable wherever no open dissection is possible for anatomical reasons or the small dimension of the fragment does not permit the use of a second independent implant. In addition to the scaphoid fracture and the scaphoid pseudoarthrosis, this is the case, for example, in the stabilization of small joint-supporting fragments, in the fusion of wrist bones or finger joints or also in the stabilization of the dens fracture of the second cervical vertebra.

The object of the present invention, in addition to the axial fixing, is now to guarantee a sufficient rotational stability about the axis of the implant even in the treatment of fractures of smaller bones, wherein the above-mentioned problems are to be avoided.

To attain this object, a hone screw set of the type mentioned at the outset is further developed according to the invention in that the first bone screw is preferably embodied as a compression screw and the first and the second bone screw have engagement means interacting with one another in order to fix the second bone screw in a position, with at least one partial region of the same protruding from the cross section of the first bone screw, relative to the first bone screw. Because the first and the second bone screw have engagement means interacting with one another, it is possible to fix the relative position of the two bone screws with respect to one another through the interaction of the two screws, so that the fixing forces do not need to be applied by the surrounding bone material. Because the second bone screw can be fixed in a position, with at least one partial region of the same protruding from the cross section of the first bone screw, relative to the first bone screw, the resulting overall cross section of the implant, comprising a first and a second screw, after the insertion of the first bone screw can be selected such that the cross section of the inserted implant is asymmetrical or not rotationally symmetrical without the placement of transverse bores so that a twisting of the two bone fragments with respect to one another is prevented.

Advantageously, the hone screw set is hereby further developed such that the engagement means interacting with one another are formed by a thread of the second bone screw and a thread of the first bone screw that can be brought into engagement therewith. In the case of an embodiment of this type, after the placement of the first bone screw, at the most a thin channel could be drilled into the bone along the outer envelope curve of the first bone screw, into which a self-cutting second screw, for example, is placed, which can be screwed into the bone along the first screw, in order in this manner to prevent a rotation of the bone fragments with respect to one another. A self-cutting second screw would be preferred that channels its path by itself when being screwed in and thereby develops a fixing radial spreading force. The first and the second bone screw can thereby be advantageously fixed with respect to one another in a position arranged essentially parallel to one another.

According to a particularly preferred embodiment of the present invention, the bone screw set is further developed in that the first bone screw has a longitudinal groove on its outer circumference, which longitudinal groove is provided with an internal thread preferably at least over a part of its length. In the case of an embodiment of this type, the second bone screw can engage with its external thread into the thread of the first bone screw screwed into the longitudinal groove of the first screw, so that, after the placement of the two screws, an overall cross section of the implant assembled from two circles overlapping one another results, whereby a rotation of the bone fragments is prevented. The longitudinal groove on the first bone screw hereby extends, for example, from the root of the screw in the direction of the tip of the screw. Since the first screw comes to rest in a completely intra-osseous manner, and the screw root thereof is thus not visible to the operator, a guide aid for drilling and placing the second screw via one and the same access is necessary. This can be fixed to the first screw or to the screw driver of the first screw.

The invention is hereby advantageously developed such that the depth of the longitudinal groove decreases in the direction towards the tip of the first bone screw, which makes it possible to make the cross section of the second bone screw in different axial regions of the implant protrude to differing extents from the virtual circular cross section of the first bone screw that would result if the totality of longitudinal groove and second screw were not provided.

If the depth of the longitudinal groove decreases by increasing the thread profile height in the direction of the tip of the first bone screw, and in addition the core diameter of the second bone screw increases towards the root, the longitudinal axis of the second bone screw is distanced during the insertion of the same and in particular towards the end of the screwing-in operation from the longitudinal axis of the first bone screw, whereby a spreading force is exerted.

The bone screw set can preferably also be further developed in such the thread of the second screw is flattened at the tip as well as at the root, in order additionally to cause a distancing of the cross sections of the first and second screw during the last rotations through the advancement of the second screw in the longitudinal direction. The second screw would thereby protrude from the circular cross section of the first screw increasingly during the last rotations and compress the surrounding osseous tissue. The bone screw set would thereby form a firmer anchoring with the surrounding osseous tissue in order in turn to achieve an increased rotational stability for the bone fragments.

In an alternative embodiment, the bone screw set according to the invention can be further developed in that the first bone screw has a through hole for accommodating the second bone screw, the axis of which forms an acute angle, in particular 10 to 40°, with the screw axis of the first bone screw. In this type of arrangement a particularly strong safeguard against twisting is achieved, wherein the second screw completely penetrates the first and in all an x-shaped overall cross section of the implant used results. The device according to the invention can hereby advantageously be further developed in that the through hole has an internal thread for screwing in the second hone screw, whereby in turn the surrounding bone material is kept free from the forces for the relative fixing of the two screws to one another.

In a preferred manner the bone screw set according to the invention is further developed in that the diameter of the first bone screw is larger than the diameter of the second bone screw, preferably 1.5-2.5 times the diameter of the second bone screw.

Advantageously, the bone screw set according to the invention is further developed in that the first bone screw is embodied in a conical manner. It is achieved by the placement of a conical bore in the bone fragments to be connected to one another and the subsequent placement of a conical screw and in particular of a compression screw, that the region of the tip of the screw does not come into engagement with the proximal bone fragment during the insertion of the screw, which in particular when, as is customary with compression screws, self-cutting threads are used, would lead to a disadvantageous change in the bore surface in the bone for the following thread part actually provided for this region.

Advantageously, the bone screw set according to the invention is further developed in that to achieve a compression the thread lead of the external thread of the first bone screw is selected to be smaller in the region of the screw root than in the region of the tip of the screw, which means that towards the end of screwing the compression screw into the set bone fragments, the proximal bone fragment is pressed onto the distal bone fragment, which is generally considered to be desirable for an acceleration of the healing process.

The invention can preferably be further developed in that the first and the second bone screw have a self-cutting external thread, whereby one bore is sufficient to guide the compression screw and to anchor it into the bone fragments. The cutting of a separate thread with the aid of a corresponding additional tool is not necessary in this case.

According to a preferred embodiment of the present invention, the bone screw set is further developed in that the second bone screw has a unthreaded region at the root.

Preferably, the invention is further developed in that the second bone screw is embodied as an unthreaded insert bolt (splint), which is embodied, e.g., in a hollow manner and with slit ends, and can be wedged after positioning by the insertion of a fitting pin.

According to a preferred embodiment of the present invention, the bone screw set is further developed in that the first bone screw is embodied in a slit manner and has anti-rotation elements that can be pressed out. The anti-rotation elements are thereby in particular pressed out by the insertion of the second screw or of a pin.

Advantageously, the bone screw set according to the present invention has a plurality of bone screws interacting with one another, wherein the first and further bone screws have engagement means interacting with one another, in order to fix the further bone screws in a position, protruding with at least one partial region of the same out of the cross section of the first bone screw, relative to the first bone screw. With a set of this type, several screws can be arranged relative to the first screw, so that it is possible to further change the cross section of the total implant in order to guarantee a further securing of the bone fragments against rotation.

The method according to the invention for the fusion of two bone fragments, in particular for treating a scaphoid fracture, using a bone screw set, comprising a first bone screw and a second bone screw, wherein the first bone screw is embodied as a compression screw and the first and the second bone screw have engagement means interacting with one another, comprises the following steps:

Setting the bone fragments

Placing a target drill wire

Drilling via the target drill wire through the two bone fragments to be connected to one another.

Screwing the first bone screw into the two bone fragments, in order to press the fracture surfaces of the bone fragments in the set position against one another, Insertion of the second bone screw into the bone fragments along an axis different from the axis of the first bone screw, wherein the second bone screw comes to rest in a recess of the first bone screw, and bringing the engagement means of the first and the second bone screw into engagement, in order to fix the second bone screw in a position, protruding with at least a partial region of the same out of the cross section of the first bone screw, relative to the first bone screw.

Setting the bone fragments and placing the bore are carried out according to known methods. hi general, the placement of the bore is carried out with a drill wire, onto which the first bone screw, which has a center bore, is pushed, so that after the bore has been made, it can be guided in a sliding manner to the face of the bore and screwed into the bone. The first bone screw is hereby inserted so far as to obtain the desired compression effect, whereupon the second bone screw is inserted into the recess of the first bone screw so that the engagement means of the first and the second bone screw come into engagement and the second bone screw penetrates into the bone along the first bone screw or protruding from the first bone screw penetrates into the bone. When the second bone screw has been brought into its target position, the entire implant has a cross section to the longitudinal axis that is not rotationally symmetrical, so that a twisting of the two bone fragments with respect to one another is prevented.

The invention is described in more detail below based on exemplary embodiments shown diagrammatically in the drawing. Therein FIG. 1 shows a first exemplary embodiment of the present invention, in which the engagement means of the first and the second bone screw are respectively formed by external threads, FIG. 2 shows a first bone screw, in which the engagement means are formed by an internal thread lying in a longitudinal groove, FIG. 3 shows the exemplary embodiment from FIG. 2 before and FIG. 4 after the complete screwing-in of the second bone screw, and FIG. 5 shows a further embodiment of the present invention in which the engagement means of the first bone screw are formed in a recess, which completely penetrates the first bone screw.

In FIG. 1 a first bone screw is labeled by 1 and a second bone screw is labeled by 2. The first bone screw 1 has a self-cutting thread, which has different screw pitches in different axial partial regions 3 and 4, so that during screwing the bone screw 1 into the bone a compression of the bone fragments occurs. During screwing-in, the bone screw 1 is guided by a drill wire 5, with which the bore is placed into the bone fragments to be fixed. After the screwing-in of the first bone screw 1, the second bone screw 2 can be screwed in along this, wherein in this case, due to the fact that the thread pitch height is different in the axial partial regions 3 and 4, the second bone screw 2 is embodied without a thread in a distal region 6 and only in the proximal region 7 engages with an external thread into the thread of the first bone screw 1. When the two bone screws of the bone screw set according to the present invention are inserted in this manner, the result is that the overall cross section transverse to the longitudinal axis of the two screws is not rotationally symmetrical, and thus a twisting of the fixed bone fragments about the longitudinal axis of the screws is prevented.

Figure 2:
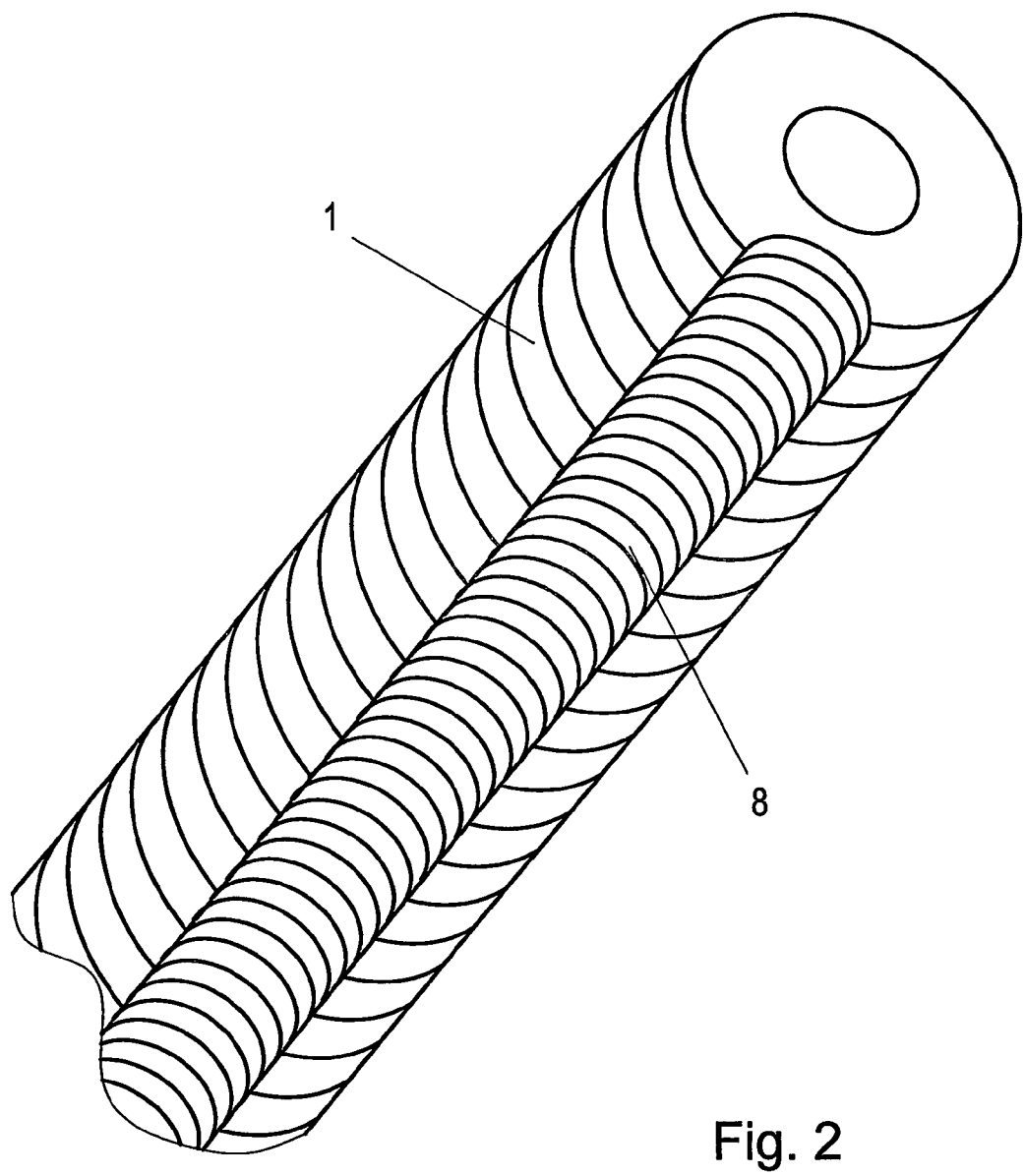
Figure 3:
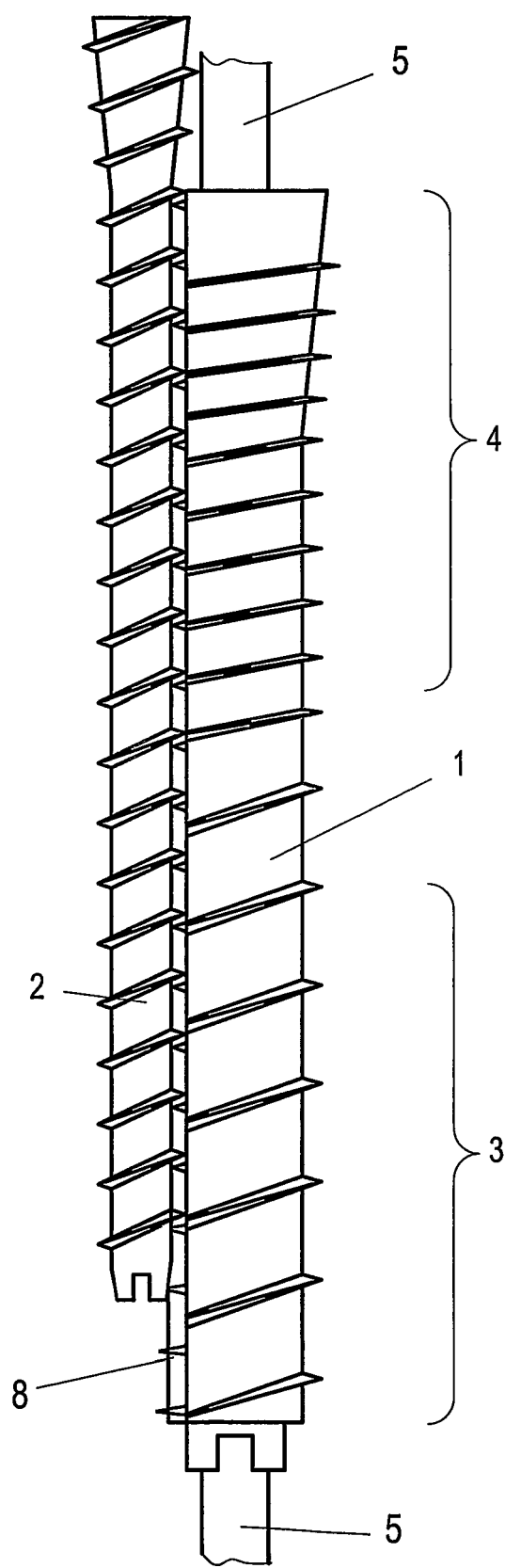
Figure 4:
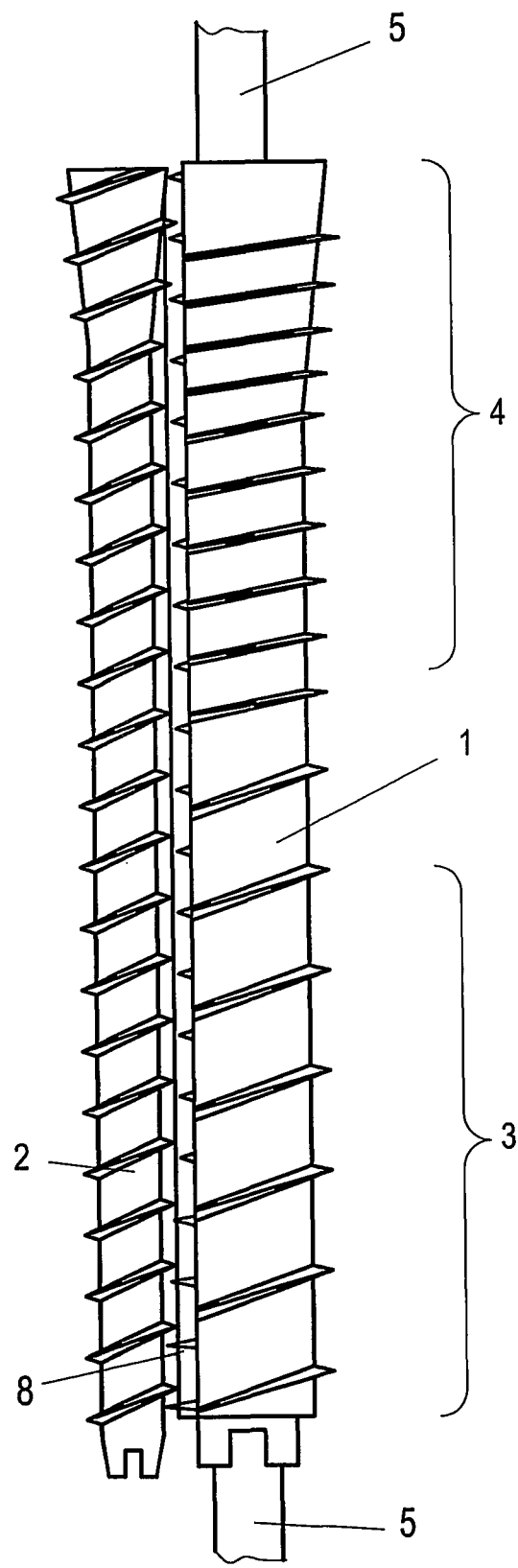

FIG. 2 in turn shows a first bone screw 1, wherein the first bone screw 1 in this case bears a longitudinal groove 8, into which an internal thread is turned. The external thread of the bone screw 1 is in turn embodied as a thread with different screw pitches and thus as a compression thread, whereas the internal thread in the longitudinal groove 8 is embodied with a constant screw pitch. After the placement of the first bone screw 1, a second bone screw 2 can be inserted, possibly also without the placement of an auxiliary bore along the longitudinal groove 8, into the thread of the longitudinal groove 8 and drilled along the bone screw 1 likewise into the bone. It is obvious that after the insertion of the second bone screw 2 into the longitudinal groove 8, a part of the cross section of the second bone screw 2 protrudes from the virtual circular envelope curve of the first bone screw 1, so that in all a cross section results that is not rotationally symmetrical, whereby the twisting of the bone fragments with respect to one another in turn is prevented. This effect is intensified by an additional compression of the surrounding osseous tissue, in that the longitudinal axis of the second bone screw, through the screwing-in of the same, is distanced from the longitudinal axis of the first bone screw. This is achieved in that, as can be seen in FIG. 4, the profile height of the through internal thread in the longitudinal groove of the first bone screw increases in the region of the screw tip, and the core diameter of the second bone screw continuously increases at the root thereof. It is discernible in FIG. 4 that in the inserted condition through the increase in the thread profile height of the first screw in the distal region and through the increase of the core diameter of the second screw in the proximal region, a distancing of the longitudinal axes of the two screws in the end phase of the insertion of the second screw takes place.

Figure 5:
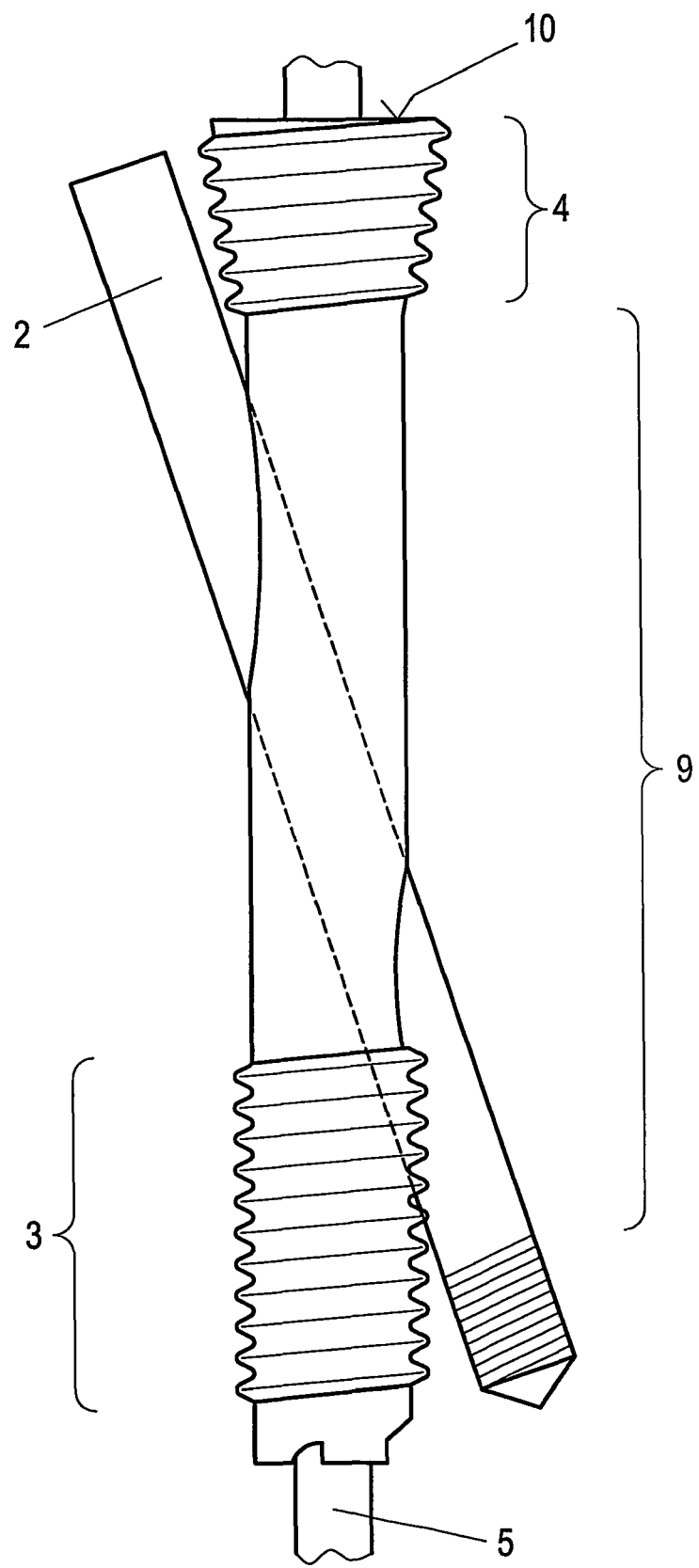

FIG. 5 shows a special embodiment of the present invention, in which the bone screw 1 has axial partial regions 3 and 4 separated from one another with threads of different screw pitch. The first bone screw 1 thus acts again as a compression screw, wherein a through hole for the accommodation of the second bone screw 2 is provided in a center partial region 9, which through hole runs at an acute angle through the bone screw 1. The angle of the through hole relative to the longitudinal axis of the first bone screw 1 is hereby selected such that the opening of the through hole opens as close as possible to the root 9 of the first bone screw 1, so that the placement of the second bone screw 2 can be carried out from the same side from which the first bone screw 1 was placed. Since the bone screw 1 is recessed completely into bone and soft part, the placement of the bone screw 2 is facilitated by the use of a targeting device, which, for example, can be attached to or placeable on the screwdriver for the bone screw 1.

What is claimed is:

1. Bone screw set comprising:
a first bone screw being a compression screw having: (a) a first thread with different screw pitches in different axial partial regions of the compression screw and (b) a root and a tip, wherein the first bone screw has, extending along an entire length of the first bone screw from the root to the tip, a longitudinal groove on its outer circumference, wherein the longitudinal groove (a) is provided with an internal thread at least over a part of its length and (b) shallows out in a region of the internal thread adjacent to the tip of the first bone screw,
at least one second bone screw having a second thread configured to interact with the internal thread,
wherein, in top view from the root to the tip, at least one partial region of the at least one second bone screw protrudes from a cross section of the first bone screw, and the first and at least one second bone screws have an overall cross section of two circles overlapping one another.

2. The bone screw set according to claim 1, wherein the first bone screw and each of the at least one second bone screws are fixed with respect to one another in a position essentially parallel to one another.

3. The bone screw set according to claim 1, wherein a depth of the longitudinal groove decreases in a direction towards the tip of the first bone screw.

4. The bone screw set according to claim 1, wherein a diameter of the first bone screw is larger than a diameter of the at least one second bone screw.

5. The bone screw set according to claim 4, wherein the diameter of the first bone screw is 1.5-2.5 times the diameter of the at least one second bone screw.

6. The bone screw set according to claim 1, wherein the first bone screw is conical.

7. The bone screw set according to claim 1, wherein, to achieve a compression, a thread lead of the first thread of the first bone screw is selected to be smaller in a region adjacent to the root of the first bone screw than in a region adjacent to the tip of the first bone screw.

8. The bone screw set according to claim 1, wherein the first thread and the second thread each are self-cutting and external.

9. The bone screw set according to claim 1, wherein the at least one second bone screw comprises a plurality of further bone screws, and wherein the plurality of further bone screws interact with the first bone screw, in order to fix each of the further bone screws in a position relative to the first bone screw, and the at least one partial region of each of the further bone screws protrudes out of the cross section of the first bone screw.

10. The bone screw set according to claim 1, wherein the first thread of the first bone screw is a continuous thread.

11. Bone screw set comprising:
- a first bone screw being a compression screw having a first thread with different screw pitches in different axial partial regions of the compression screw, wherein the first bone screw has a longitudinal groove on its outer circumference, wherein the longitudinal groove is provided with an internal thread at least over a part of its length, wherein a thread profile height of the internal thread increases in a direction of a tip of the first bone screw,
- at least one second bone screw having a second thread, wherein a core diameter of the at least one second bone screw increases towards a root of the at least one second bone screw,
- wherein at least one partial region of the at least one second bone screw protrudes from a cross section of the first bone screw, and wherein the first bone screw and each of the at least one second bone screw are fixed with respect to one another in a position essentially parallel to one another.

* * * * *